US012577569B2

(12) United States Patent
Rupp et al.

(10) Patent No.: US 12,577,569 B2
(45) Date of Patent: Mar. 17, 2026

(54) APTAMERS FOR THE REVERSIBLE INHIBITION OF DNA POLYMERASES

(71) Applicant: INTEGRATED DNA TECHNOLOGIES, INC., Coralville, IA (US)

(72) Inventors: Susan Marie Rupp, Marion, IA (US); Shambhavi Shubham, Coralville, IA (US); Scott Rose, Coralville, IA (US); Brianna Cagle, Iowa City, IA (US)

(73) Assignee: INTEGRATED DNA TECHNOLOGIES, INC., Coralville, IA (US)

( * ) Notice: Subject to any disclaimer, the term of this patent is extended or adjusted under 35 U.S.C. 154(b) by 637 days.

(21) Appl. No.: 18/057,614

(22) Filed: Nov. 21, 2022

(65) Prior Publication Data

US 2023/0102276 A1     Mar. 30, 2023

Related U.S. Application Data

(60) Provisional application No. 63/281,872, filed on Nov. 22, 2021.

(51) Int. Cl.
| | |
|---|---|
| *C12Q 1/68* | (2018.01) |
| *C12N 15/115* | (2010.01) |
| *C12Q 1/6848* | (2018.01) |
| *C12Q 1/686* | (2018.01) |

(52) U.S. Cl.
CPC .......... *C12N 15/115* (2013.01); *C12Q 1/6848* (2013.01); *C12Q 1/686* (2013.01); *C12N 2310/16* (2013.01)

(58) Field of Classification Search
None
See application file for complete search history.

(56) References Cited

U.S. PATENT DOCUMENTS 10,036,061 B2 *  7/2018  Fiss ..................... C12N 15/113

OTHER PUBLICATIONS

Smith, T. et al. "Comparison of biosequences." Advances in applied mathematics 2.4 (1981): 482-489.
Wang, T., et al. "Three decades of nucleic acid aptamer technologies: Lessons learned, progress and opportunities on aptamer development." Biotechnology advances 37.1 (2019): 28-50.
International Search Report and Written Opinion for Application No. PCT/US2022/080254 dated May 15, 2023 (12 pages).
Dang, C. et al. "Oligonucleotide inhibitors of Taq DNA polymerase facilitate detection of low copy number targets by PCR." Journal of molecular biology 264.2 (1996): 268-278.

* cited by examiner

*Primary Examiner* — Jehanne S Sitton
(74) *Attorney, Agent, or Firm* — Michael Best & Friedrich LLP

(57) ABSTRACT

Described herein are methods and compositions for improved polymerase chain reaction (PCR). In one aspect the methods and compositions include improved aptamers to reversibly inhibit polymerase and exonuclease activity of the polymerase enzyme.

15 Claims, 2 Drawing Sheets
Specification includes a Sequence Listing.

Aptamer 118640 Dissociation Curves

APTAMERS FOR THE REVERSIBLE INHIBITION OF DNA POLYMERASES

CROSS-REFERENCE TO RELATED APPLICATIONS

This application claims priority to U.S. Provisional Patent Application No. 63/281,872 filed on Nov. 22, 2021, which is incorporated by reference herein in its entirety.

REFERENCE TO SEQUENCE LISTING

This application was filed with a Sequence Listing XML in ST.26 XML format accordance with 37 C.F.R. § 1.831. The Sequence Listing XML file submitted in the USPTO Patent Center, "013670-0011-US02_sequence_listing_xml_21-NOV-2022.xml," was created on Nov. 21, 2022, contains 9 sequences, has a file size of 12.1 Kbytes, and is incorporated by reference in its entirety into the specification.

TECHNICAL FIELD

Described herein are methods and compositions for improved polymerase chain reaction (PCR) using aptamer blocked thermostable DNA polymerases. Further described herein are aptamer compositions for the reversible inhibition of thermostable DNA polymerases.

BACKGROUND

The polymerase chain reaction (PCR) is a widely used technique to detect minute quantities of DNA through exponential amplification. PCR requires a polymerase that will tolerate high temperatures (94° C. or higher) during the thermal cycling protocol. One of the most commonly used polymerases for this purpose is Taq DNA Polymerase, isolated from the thermophile *Thermus aquaticus*. Taq DNA Polymerase possesses activity, albeit reduced, at room temperature. This activity at lower temperatures can be problematic in that it leads to non-specific amplification and primer dimer formation. In contrast, during thermal cycling, non-specific binding is reduced at higher temperatures as annealing becomes more stringent. Since reaction specificity is critical for successful target amplification in PCR, this non-specific amplification of Taq DNA Polymerase at lower temperatures can lead to reduced specificity and undesirable results.

Several techniques have been employed to prevent the activity of Taq DNA Polymerase at low temperatures. One such method is physical separation of reaction components (polymerase, dNTPs, primers, etc.) until the reaction reaches a higher temperature. Once a higher temperature is reached, the user is required to open the reaction and spike-in these additional components to allow the reaction to proceed. This method is labor-intensive and contamination-prone. Subsequent methods separate reaction components through the use of wax layers, though this method is generally not widely used.

More recent methods that are used today involve the use of enzyme interactions to block activity. A popular approach to this method is through the use of an antibody specific to Taq DNA Polymerase. The antibody renders Taq inactive at low temperature but denatures from the protein and dissociates during the initial denaturation step at high temperature. Several disadvantages of the antibody approach are cost of the antibody, maintaining consistency in batches produced and maintaining a consistent supply. Another approach is the use of chemical anhydrides to reversibly modify amino acid side chains of the polymerase. Although effective and less expensive than antibodies, chemical modification takes longer incubation times and higher temperatures to reactivate the polymerase, and only a fraction of the original activity can be restored. Both of these approaches are also limited in that antibodies and chemical anhydrides cannot rebind the enzyme at lower temperatures once dissociated.

The use of aptamers is another method to add hot start capability to enzymes and offers improvements over methods previously mentioned. Aptamers are short ssDNA or ssRNA oligonucleotides that selectively bind to specific targets, such as proteins, peptides, carbohydrates, small molecules, toxins, and live cells. Aptamers assume a variety of shapes due to the tendency to form helices and single-stranded loops, therefore binding is determined by the aptamer's tertiary structure. They have a long shelf life and bind with high selectivity and specificity. Aptamers are identified through a one-time selection process known as SELEX, Systematic Evolution of Ligands through Exponential Enrichment. See Wang et al., *Biotech. Adv.* 37: 28-50 (2019), which is incorporated by reference herein for such teachings. Unlike antibody and chemical methods, aptamers are capable of rebinding their targets at low temperatures. One benefit of this property is the possibility of shipping Taq DNA Polymerase containing master mixes at ambient temperatures. If the temperature increases during shipment, the aptamer will simply rebind the polymerase to render it inactive once temperatures decrease again.

Unlike prior work which involves physical separation methods, or the use of antibodies or chemical anhydrides, the current invention utilizes aptamers, which demonstrably show both exonuclease and polymerase inhibition as compared to non-hot start WT Phusion polymerase. Aptamers can be produced in-house, which lowers cost and eliminates the dependency on other suppliers.

What is needed are aptamers for the reversible inhibition of thermostable DNA polymerases.

SUMMARY

Described herein are compositions and methods for aptamer constructs and methods of PCR. The enzyme composition includes a thermostable DNA polymerase and an aptamer wherein the aptamers is selected form the group consisting of SEQ ID NO: 8 or SEQ ID NO: 9. In one aspect the DNA polymerase is a Phusion DNA polymerase. In another aspect the Phusion DNA polymerase is Pfu-sso7d.

In another embodiment the composition is an aptamer. In one aspect the aptamer is selected from the group consisting of SEQ ID NO: 8 or SEQ ID NO: 9.

In one embodiment the method includes a method for amplifying a target DNA sequence. The method includes providing a reaction mixture comprising: a DNA polymerase; a DNA polymerase aptamer selected form the group consisting of SEQ ID NO: 8 or SEQ ID NO: 9 to form a blocked DNA Polymerase; at least one oligonucleotide primer; a sample nucleic acid that may or may not have the target sequence; hybridizing the oligonucleotide primer to the target DNA sequence in the reaction mixture; elevating the temperature to release the DNA polymerase aptamer from the blocked DNA polymerase; and extending the primer with the DNA polymerase.

One embodiment described herein is a composition comprising: a thermostable DNA polymerase and an aptamer;

wherein the aptamer is selected from a nucleotide sequence comprising at least 90% identity to SEQ ID NO:8 or SEQ ID NO:9. In one aspect, the aptamer is selected from a nucleotide sequence comprising SEQ ID NO:8 or SEQ ID NO:9. In another aspect, the thermostable DNA polymerase is a Phusion DNA polymerase. In another aspect, the Phusion DNA polymerase is Pfu-sso7d.

Another embodiment described herein is an aptamer selected from a nucleotide sequence comprising at least 90% identity to SEQ ID NO:8 or SEQ ID NO:9. In one aspect, the aptamer is selected from a nucleotide sequence comprising SEQ ID NO:8 or SEQ ID NO:9.

Another embodiment described herein is a method for amplifying a target DNA sequence, said method comprising the steps of: (a) providing a reaction mixture comprising: (i) a thermostable DNA polymerase, (ii) a thermostable DNA polymerase aptamer selected from a nucleotide sequence comprising at least 90% identity to SEQ ID NO:8 or SEQ ID NO:9, wherein the thermostable DNA polymerase aptamer binds to the thermostable DNA polymerase to form a blocked thermostable DNA polymerase; (iii) at least one oligonucleotide primer, (iv) one or more sample nucleic acids that may or may not comprise a target sequence complementary to the at least one oligonucleotide primer; (b) hybridizing the at least one oligonucleotide primer to the sample nucleic acids that comprise a target DNA sequence complementary to the at least one oligonucleotide primer; (c) elevating the temperature to release the thermostable DNA polymerase aptamer from the blocked thermostable DNA polymerase; and (d) initiating DNA polymerase activity and extending the primer with the DNA polymerase. In one aspect, the thermostable DNA polymerase aptamer is selected from a nucleotide sequence comprising SEQ ID NO:8 or SEQ ID NO:9. In another aspect, the thermostable DNA polymerase is a Phusion DNA polymerase. In another aspect, the Phusion DNA polymerase is Pfu-sso7d. In another aspect, the elevated temperature to release the thermostable DNA polymerase aptamer from the blocked thermostable DNA polymerase is greater than 45° C. In another aspect, the elevated temperature to release the thermostable DNA polymerase aptamer from the blocked thermostable DNA polymerase is from 50-55° C. In another aspect, the initiating DNA polymerase activity and extending the primer with the DNA polymerase is performed at a temperature of greater than 65° C. In another aspect, the reaction mixture further comprises, a buffer mixture and dNTPs. In another aspect, the buffer mixture comprises: 10 mM Tris-HCl (pH 8.4 at 25° C.), 1.5 mM MgCl$_2$, 110 mM KCl, 0.08% (w/v) Brij-58, 0.2% (w/v) PEG-8000, and 0.1% (v/v) propylene glycol); and the dNTPs comprise 0.8 mM dNTPs.

Another embodiment described herein is a method for selecting aptamers for the reversible inhibition of a DNA polymerase, the method comprising: (a) incubating a library of aptamer sequences with one or more DNA polymerases to form aptamer-DNA polymerase complexes; (b) isolating the aptamer-DNA polymerase complexes; (c) amplifying the aptamer sequences from the aptamer-DNA polymerase complexes; (d) repeating the steps (a) to (c) a plurality of times to enrich the aptamers capable of forming aptamer-DNA polymerase complexes; and (e) sequencing the aptamer sequences to identify aptamers having DNA polymerase binding activity. In one aspect, the isolating step comprises washing under high stringency conditions.

Another embodiment described herein is an aptamer capable of the reversible inhibition of a DNA polymerase produced by the methods described herein. In one aspect, the aptamer is selected from a nucleotide sequence comprising at least 90% identity to SEQ ID NO:8 or SEQ ID NO:9. In another aspect, the aptamer is selected from a nucleotide sequence comprising SEQ ID NO:8 or SEQ ID NO:9.

Another embodiment described herein is the use of an aptamer for the reversible inhibition of a thermostable DNA polymerase.

DETAILED DESCRIPTION

Figure 1:
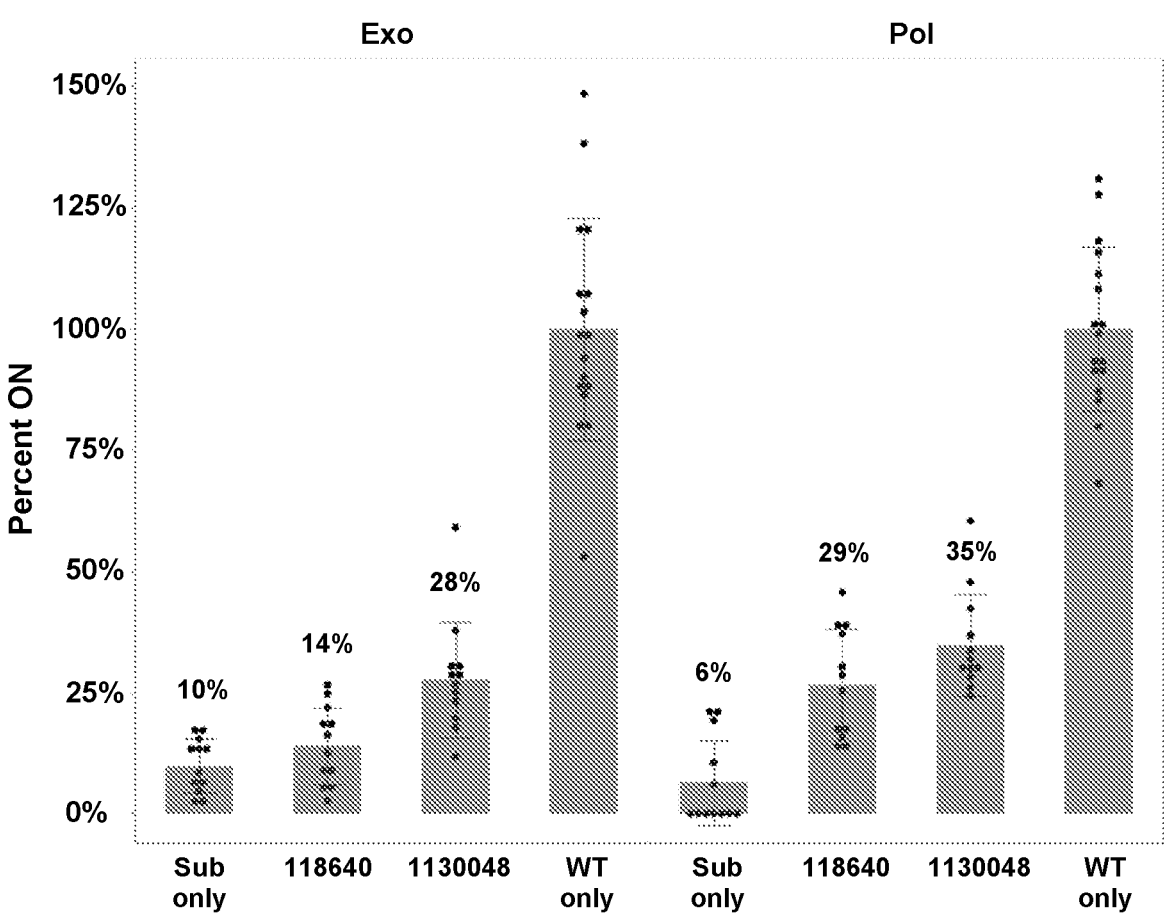
FIG. 1 shows percent activity for 3 hours at 1:3 (polymerase:aptamer) ratio. The left panel (Exo) shows exonuclease inhibition measured at 30° C. The right panel (Pol) shows polymerase inhibition measured at 45° C. Sub Only=substrate. 118640 is SEQ ID NO: 8 blocked polymerase and 1130048 is SEQ ID NO: 9 blocked polymerase, WT (non-hot start wild-type Polymerase).
Figure 2:
FIG. 2 shows aptamer dissociation from polymerase at 45° C. (top panel), 50° C. (middle panel), or 55° C. (bottom panel) measured by Relative Fluorescent Units (RFU). Assay conditions were the same as those used for Polymerase Inhibition Assay, except data was collected every 30 seconds for a total of 5.5 hours. Polymerase:Aptamer ratio 1:3 (left panel) or 1:5 ratio (right panel). Substrate only (short dashed line), Polymerase only (WT, Non-hot start Polymerase, long dashed line), Aptamer 118640+Polymerase (solid line).

Unless otherwise defined, all technical and scientific terms used herein have the same meaning as commonly understood by one of ordinary skill in the art. For example, any nomenclatures used in connection with, and techniques of biochemistry, molecular biology, immunology, microbiology, genetics, cell and tissue culture, and protein and nucleic acid chemistry described herein are well known and commonly used in the art. In case of conflict, the present disclosure, including definitions, will control. Exemplary methods and materials are described below, although methods and materials similar or equivalent to those described herein can be used in practice or testing of the embodiments and aspects described herein.

As used herein, the terms "amino acid," "nucleotide," "polynucleotide," "vector," "polypeptide," and "protein" have their common meanings as would be understood by a biochemist of ordinary skill in the art. Standard single letter nucleotides (A, C, G, T, U) and standard single letter amino acids (A, C, D, E, F, G, H, I, K, L, M, N, P, Q, R, S, T, V, W, or Y) are used herein.

As used herein, the terms such as "include," "including," "contain," "containing," "having," and the like mean "comprising." The present disclosure also contemplates other embodiments "comprising," "consisting of," and "consisting essentially of," the embodiments or elements presented herein, whether explicitly set forth or not.

As used herein, the term "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified.

As used herein, the term "or" can be conjunctive or disjunctive.

As used herein, the term "substantially" means to a great or significant extent, but not completely.

As used herein, the term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In one aspect, the term "about" refers to any values, including both integers and fractional components that are within a variation of up to ±10% of the value modified by the term "about." Alternatively, "about" can mean within 3 or more standard deviations, per the practice in the art. Alternatively, such as with respect to biological systems or processes, the term "about" can mean within an order of magnitude, in some embodiments within 5-fold, and in some embodiments within 2-fold, of a value. As used herein, the symbol "~" means "about" or "approximately."

All ranges disclosed herein include both end points as discrete values as well as all integers and fractions specified within the range. For example, a range of 0.1-2.0 includes 0.1, 0.2, 0.3, 0.4 . . . 2.0. If the end points are modified by the term "about," the range specified is expanded by a variation of up to ±10% of any value within the range or within 3 or more standard deviations, including the end points.

As used herein, the term "hybridization" refers to the process of combining two complementary single-stranded nucleic acid molecules and allowing them to form a single double-stranded hybrid molecule through base pairing.

As used herein, the term "target enrichment" with respect to a nucleic acid is intended to refer to increasing the relative concentration of particular nucleic acid species in the sample.

As used herein, the term "nucleic acid" may refer to DNA, RNA, dsDNA, dsRNA, ssDNA, ssRNA, or hybrids of DNA/RNA complexes or sequences obtained from any source, containing target and non-target sequences. For example, a nucleic acid sample can be obtained from artificial sources or by chemical synthesis, or from viruses, prokaryotic cells including microbes, or eukaryotic cells. Biological samples may be vertebrate, including human or excluding humans, invertebrates, plants, microbes, viruses, *Mycoplasma*, fungi, or Archaea.

A nucleic acid sample may comprise whole genomic sequences, portions of the genomic sequence, chromosomal sequences, mitochondrial sequences, PCR products, whole genome amplification products or products of other amplification protocol, such as but not limited to, cDNA sequences, mRNA sequences, whole transcriptome sequences, exons, or intronic. These examples are not to be construed as limiting the sample types applicable to aspects described herein.

Described herein are methods and compositions for improved Polymerase Chain Reaction (PCR) using aptamer blocked polymerases. Further described herein are ssDNA Taq DNA Polymerase aptamer candidates identified through SELEX. A SELEX experiment typically begins with a library of up to 10^15 different target nucleic acid strands, which are exposed to various selection pressures that enrich for the best target binding sequences. These target sequences are amplified by PCR and the enriched library is used in the next selection cycle. The aptamer candidates described here would allow a low-cost alternative to antibody hot start, can be produced in large quantities in-house, and have a long shelf life.

Described herein are methods and compositions to render both polymerase activity and exonuclease activity of Phusion DNA Polymerase inactive at low temperatures. The aptamer selection process can produce an aptamer in-house at low cost and which has long shelf-life. Upon increased temperate the aptamer is released, and the polymerase regains activity. Unlike antibodies and chemical modifications that render polymerases hot start, aptamers have the unique ability to rebind at low temperatures. This ability allows master mixes containing hot start Phusion DNA Polymerase to be shipped at ambient temperature. It also eliminates undesired polymerase activity after reaction completion that could otherwise affect baseline reads in negative samples.

One embodiment described herein is a composition comprising an aptamer blocked DNA polymerase. In one aspect the aptamer is a nucleotide sequence comprising a sequence comprising 90 to 100% identity to SEQ ID NO: 8 or SEQ ID NO: 9. In one aspect, the nucleotide sequence comprises SEQ ID NO: 8 or SEQ ID NO: 9, In another aspect the aptamer reversibly inactivates both the polymerase activity and exonuclease activity of Phusion DNA polymerase.

One embodiment described herein is a composition comprising: a thermostable DNA polymerase and an aptamer; wherein the aptamer is selected from a nucleotide sequence comprising at least 90% identity to SEQ ID NO:8 or SEQ ID NO:9. In one aspect, the aptamer is selected from a nucleotide sequence comprising SEQ ID NO:8 or SEQ ID NO:9. In another aspect, the thermostable DNA polymerase is a Phusion DNA polymerase. In another aspect, the Phusion DNA polymerase is Pfu-sso7d.

Another embodiment described herein is an aptamer selected from a nucleotide sequence comprising at least 90% identity to SEQ ID NO:8 or SEQ ID NO:9. In one aspect, the aptamer is selected from a nucleotide sequence comprising SEQ ID NO:8 or SEQ ID NO:9.

Another embodiment described herein is a method for amplifying a target DNA sequence, said method comprising the steps of: (a) providing a reaction mixture comprising: (i) a thermostable DNA polymerase, (ii) a thermostable DNA polymerase aptamer selected from a nucleotide sequence comprising at least 90% identity to SEQ ID NO:8 or SEQ ID NO:9, wherein the thermostable DNA polymerase aptamer binds to the thermostable DNA polymerase to form a blocked thermostable DNA polymerase; (iii) at least one oligonucleotide primer, (iv) one or more sample nucleic acids that may or may not comprise a target sequence complementary to the at least one oligonucleotide primer; (b) hybridizing the at least one oligonucleotide primer to the sample nucleic acids that comprise a target DNA sequence complementary to the at least one oligonucleotide primer; (c) elevating the temperature to release the thermostable DNA polymerase aptamer from the blocked thermostable DNA polymerase; and (d) initiating DNA polymerase activity and extending the primer with the DNA polymerase. In one aspect, the thermostable DNA polymerase aptamer is selected from a nucleotide sequence comprising SEQ ID NO:8 or SEQ ID NO:9. In another aspect, the thermostable DNA polymerase is a Phusion DNA polymerase. In another aspect, the Phusion DNA polymerase is Pfu-sso7d. In another aspect, the elevated temperature to release the thermostable DNA polymerase aptamer from the blocked thermostable DNA polymerase is greater than 45° C. In another aspect, the elevated temperature to release the thermostable DNA polymerase aptamer from the blocked thermostable DNA polymerase is from 50-55° C. In another aspect, the initiating DNA polymerase activity and extending the primer with the DNA polymerase is performed at a temperature of greater than 65° C. In another aspect, the reaction mixture further comprises, a buffer mixture and dNTPs. In another aspect, the buffer mixture comprises: 10 mM Tris-HCl (pH 8.4 at 25° C.), 1.5 mM MgCl$_2$, 110 mM KCl, 0.08% (w/v) Brij-58, 0.2% (w/v) PEG-8000, and 0.1% (v/v) propylene glycol); and the dNTPs comprise 0.8 mM dNTPs.

Another embodiment described herein is a method for selecting aptamers for the reversible inhibition of a DNA polymerase, the method comprising: (a) incubating a library of aptamer sequences with one or more DNA polymerases to form aptamer-DNA polymerase complexes; (b) isolating the aptamer-DNA polymerase complexes; (c) amplifying the aptamer sequences from the aptamer-DNA polymerase complexes; (d) repeating the steps (a) to (c) a plurality of times to enrich the aptamers capable of forming aptamer-DNA polymerase complexes; and (e) sequencing the aptamer sequences to identify aptamers having DNA polymerase binding activity. In one aspect, the isolating step comprises washing under high stringency conditions.

Another embodiment described herein is an aptamer capable of the reversible inhibition of a DNA polymerase produced by the methods described herein. In one aspect, the aptamer is selected from a nucleotide sequence comprising at least 90% identity to SEQ ID NO:8 or SEQ ID NO:9. In another aspect, the aptamer is selected from a nucleotide sequence comprising SEQ ID NO:8 or SEQ ID NO:9.

Another embodiment described herein is the use of an aptamer for the reversible inhibition of a thermostable DNA polymerase.

Another embodiment described herein is a process or means for manufacturing one or more of the nucleotide sequence described herein, the process comprising: transforming or transfecting a cell with a nucleic acid comprising a nucleotide sequence described herein; growing the cells; optionally isolating additional quantities of a nucleotide sequence described herein; inducing expression of a polypeptide encoded by a nucleotide sequence of described herein; isolating the polypeptide encoded by a nucleotide described herein.

Another embodiment described herein is a nucleotide sequence produced by the methods or means described herein.

Another embodiment described herein is a research tool comprising a nucleotide sequence described herein.

Another embodiment described herein is a reagent comprising a nucleotide sequence described herein.

Another embodiment described herein is a polynucleotide vector comprising one or more nucleotide sequences described herein.

Another embodiment described herein is a cell comprising one or more nucleotide sequences described herein or a polynucleotide vector described herein.

Further embodiments described herein include nucleic acid molecules comprising polynucleotides having nucleotide sequences comprising sequences having about 50%, 55%, 60%, 65%, 70%, 75%, 80%, 85%, 90%, 91%, 92%, 93%, 94%, 95%, 96%, 97%, 98%, or 99% identity, and more preferably at least about 90-99% or 100% identity to (a) nucleotide sequences in SEQ ID NO: 8 or 9; or (b) nucleotide sequences capable of hybridizing to SEQ ID NO: 8 or 9.

By a polynucleotide having a nucleotide sequence at least, for example, 90-99% "identical" to a reference nucleotide sequence of SEQ ID NO: 8 or 9 is intended that the nucleotide sequence of the polynucleotide be identical to the reference sequence except that the polynucleotide sequence can include up to about 10 to 1 point mutations, additions, or deletions per each 100 nucleotides of the reference nucleotide sequence without affecting the function or activity of the polynucleotide sequence.

In other words, to obtain a polynucleotide having a nucleotide sequence about at least 90-99% identical to a reference nucleotide sequence, up to 10% of the nucleotides in the reference sequence can be deleted, added, or substituted, with another nucleotide, or a number of nucleotides up to 10% of the total nucleotides in the reference sequence can be inserted into the reference sequence. These mutations of the reference sequence can occur at the 5'- or 3'-terminal positions of the reference nucleotide sequence or anywhere between those terminal positions, interspersed either individually among nucleotides in the reference sequence or in one or more contiguous groups within the reference sequence.

As noted above, two or more polynucleotide sequences can be compared by determining their percent identity. The percent identity of two sequences is generally described as the number of exact matches between two aligned sequences divided by the length of the shorter sequence and multiplied by 100. An approximate alignment for nucleic acid sequences is provided by the local homology algorithm of Smith and Waterman, *Advances in Applied Mathematics* 2: 4 82-489 (1981).

The polynucleotides described herein include those comprising mutations, variations, substitutions, additions, deletions, and particular examples of the polynucleotides described herein. In addition, the polynucleotides can be ribonucleotides (RNA), deoxyribonucleotides (DNA), or combinations thereof, where the sequence comprise one or more ribonucleotides, or deoxyribonucleotides. The sequences can comprise ribonucleotides with for example ribothymidine nucleotides instead of uridine nucleotides to maintain consonance with the analogous DNA sequence.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the foregoing discussion discloses and describes merely exemplary embodiments. All patents and publications cited herein are incorporated by reference herein for the specific teachings thereof.

Various embodiments and aspects of the inventions described herein are summarized by the following clauses:

Clause 1. A composition comprising:

a thermostable DNA polymerase and an aptamer;

wherein the aptamer is selected from a nucleotide sequence comprising at least 90% identity to SEQ ID NO:8 or SEQ ID NO:9.

Clause 2. The composition of clause 1, wherein the aptamer is selected from a nucleotide sequence comprising SEQ ID NO:8 or SEQ ID NO:9.

Clause 3. The composition of clause 1 or 2, wherein the thermostable DNA polymerase is a Phusion DNA polymerase.

Clause 4. The composition of clause 2 wherein the Phusion DNA polymerase is Pfu-sso7d.

Clause 5. An aptamer selected from a nucleotide sequence comprising at least 90% identity to SEQ ID NO:8 or SEQ ID NO:9.

Clause 6. The aptamer of clause 5, wherein the aptamer is selected from a nucleotide sequence comprising SEQ ID NO:8 or SEQ ID NO:9.

Clause 7. A method for amplifying a target DNA sequence, said method comprising the steps of:

(a) providing a reaction mixture comprising:

(i) a thermostable DNA polymerase, (ii) a thermostable DNA polymerase aptamer selected from a nucleotide sequence comprising at least 90% identity to SEQ ID NO:8 or SEQ ID NO:9, wherein the thermostable DNA polymerase aptamer binds to the thermostable DNA polymerase to form a blocked thermostable DNA polymerase;

(iii) at least one oligonucleotide primer, (iv) one or more sample nucleic acids that may or may not comprise a target sequence complementary to the at least one oligonucleotide primer;

(b) hybridizing the at least one oligonucleotide primer to the sample nucleic acids that comprise a target DNA sequence complementary to the at least one oligonucleotide primer;

(c) elevating the temperature to release the thermostable DNA polymerase aptamer from the blocked thermostable DNA polymerase; and (d) initiating DNA polymerase activity and extending the primer with the DNA polymerase.

Clause 8. The method of clause 7, wherein the thermostable DNA polymerase aptamer is selected from a nucleotide sequence comprising SEQ ID NO:8 or SEQ ID NO:9.

Clause 9. The method of clause 7 or 8, wherein the thermostable DNA polymerase is a Phusion DNA polymerase.

Clause 10. The method of clause 9, wherein the Phusion DNA polymerase is Pfu-sso7d.

Clause 11. The method of any one of clauses 7-10, wherein the elevated temperature to release the thermostable DNA polymerase aptamer from the blocked thermostable DNA polymerase is greater than 45° C.

Clause 12. The method of any one of clauses 7-11, wherein the elevated temperature to release the thermostable DNA polymerase aptamer from the blocked thermostable DNA polymerase is from 50-55° C.

Clause 13. The method of any one of clauses 7-12, wherein the initiating DNA polymerase activity and extending the primer with the DNA polymerase is performed at a temperature of greater than 65° C.

Clause 14. The method of any one of clauses 7-13, wherein the reaction mixture further comprises, a buffer mixture and dNTPs.

Clause 15. The method of any one of clauses 7-14, wherein:

the buffer mixture comprises: 10 mM Tris-HCl (pH 8.4 at 25° C.), 1.5 mM $MgCl_2$, 110 mM KCl, 0.08% (w/v) Brij-58, 0.2% (w/v) PEG-8000, and 0.1% (v/v) propylene glycol); and the dNTPs comprise 0.8 mM dNTPs.

Clause 16. A method for selecting aptamers for the reversible inhibition of a DNA polymerase, the method comprising:

(a) incubating a library of aptamer sequences with one or more DNA polymerases to form aptamer-DNA polymerase complexes;

(b) isolating the aptamer-DNA polymerase complexes;

(c) amplifying the aptamer sequences from the aptamer-DNA polymerase complexes;

(d) repeating the steps (a) to (c) a plurality of times to enrich the aptamers capable of forming aptamer-DNA polymerase complexes; and (e) sequencing the aptamer sequences to identify aptamers having DNA polymerase binding activity.

Clause 17. The method of clause 16, wherein the isolating step comprises washing under high stringency conditions.

Clause 18. An aptamer capable of the reversible inhibition of a DNA polymerase produced by the method of clause 16 or 17.

Clause 19. The aptamer of clause 18, wherein the aptamer is selected from a nucleotide sequence comprising at least 90% identity to SEQ ID NO:8 or SEQ ID NO:9.

Clause 20. The aptamer of clause 18, wherein the aptamer is selected from a nucleotide sequence comprising SEQ ID NO:8 or SEQ ID NO:9.

Clause 21. Use of an aptamer for the reversible inhibition of a thermostable DNA polymerase.

EXAMPLES

Example 1

Phusion Aptamer Candidate Selection

This example demonstrates selection of aptamers to inhibit both the polymerase activity and exonuclease activity of polymerases.

The SELEX process consists of binding a library of single stranded aptamers to an immobilized target. Unbound sequences are washed, and the sequences bound to the target are eluted. Once eluted sequences are collected, they are amplified via PCR and converted to ssDNA for use in the next round of selection. The rounds of selection are repeated (generally 5-10 times). Following the final round of selection, the sequences are sequenced and analyzed for enrichment of sequences with the greatest affinity for the target molecule.

To select for inhibitory sequences against the Phusion polymerase (PFU-sso7d fusion) two different approaches for selection were performed against three different targets. The three target polymerases were Wild-type (WT), exonuclease mutant (D215A) and polymerase mutant Phusion polymerase (D405A). For selection, an aptamer library was used. The library consisted of a plurality of oligonucleotides (nucleic acid library) containing a 40-nucleotide random region flanked by a constant priming region (see Table 1, SEQ ID NO: 1). SEQ ID NO: 1 contains a 40-nucleotide random region ($N_{40}$) flanked by the two constant priming regions.

(A) Selection Strategy 1

First, selection included two different target polymerases (WT polymerase and polymerase with inactivated exonuclease domain). For both of these targets three different selection conditions were used.

1. Selection Criteria 1

Targets were incubated with the nucleic acid library solely in 1× HiFi Buffer (1× HiFi IDT Buffer #3: 10 mM Tris-HCl (pH 8.4 at 25° C.); 1.5 mM MgCl₂; 110 mM KCl; 0.08% (w/v) Brij-58; 0.2% (w/v) PEG-8000; and 0.1% (v/v) propylene glycol) (Integrated DNA Technologies, Inc, Coralville, IA) and the bound complexes were washed with 1× HiFi Buffer.

2. Selection Criteria 2

Targets were incubated with the nucleic acid library in the presence of 0.5 mM dextran sulfate and the bound complexes were washed with 1× HiFi Buffer.

3. Selection Criteria 3

Targets were incubated with the nucleic acid library in 1× HiFi Buffer without any competitor (Dextran) but the bound complex was washed with 2 mM Dextran Sulfate.

(B) Selection Strategy 2

Whereas for the second selection three target polymerases were used (WT polymerase, polymerase with inactivated exonuclease domain, and polymerase with active exonuclease domain but an inactivated polymerase domain). For this selection, complexes were incubated with targets in 1× buffer without any competitor or with dextran sulfate included in the washes.

Five rounds of SELEX were completed for each of the above selection strategies. Each SELEX round began with folding the aptamer in a polymerase storage buffer and incubating the folded aptamer library for 1 hour with Phusion DNA polymerase (Integrated DNA Technologies, Inc., Coralville, IA) at 45° C. Post binding the polymerase-DNA aptamer complex was immobilized on Dynabeads (Thermo Fisher Scientific, Waltham, MD). Stringency during selections was enhanced by increasing the washes in each round and changing the protein to DNA ratio. Bound fractions were amplified using primers indicated in Table 1 (SEQ ID NO: 2 and SEQ ID NO: 3) and converted to ssDNA using lambda exonuclease (New England Biolabs, Ipswich, MA). The converted ssDNA library was then used as the starting material for the pooled nucleic acid library in the next round of selection. After each subsequent round of amplification, an aliquot was saved. At the end of five rounds of selection, amplified material was sequenced on the Illumina Mi-Seq platform. Sequence analysis was performed via AptaSuite to identify sequences that showed enrichment.

After sequencing analysis 120 sequences were obtained from the 5 rounds of SELEX selection and tested for their inhibition against the polymerase's polymerase activity and the polymerases exonuclease activity separately.

TABLE 1

Sequences used for Example 1

| SEQ ID NO: | NAME | SEQUENCE |
|---|---|---|
| 1 | Pool B Pfu | GTTCAGTCCCTACGGCGCTAAC (N₄₀) GCCACCGTGCTACAACCAAG |

TABLE 1-continued

Sequences used for Example 1

| SEQ ID NO: | NAME | SEQUENCE |
|---|---|---|
| 2 | SELEX pool B Fwd primer | /56-FAM/GTTCAGTCCCTACGG CGCTAAC |
| 3 | SELEX pool B Rev primer | /5Phos/CTTGGTTGTAGCACGGT GGC |
| 4 | PE pol Inhib FOR | TCTCCAAGTTGTGGCGTC |
| 5 | PE_pol_ Inhib_1 | /5IABkFQ/TCCTCCTCTTTTTTT GAGGAGG/iFluorT/CTTGGTAA ACGATCGGACGCCACAACTTGCAG AAACTAGAACATTGATAATTTTAC TGGCGATGTCAATAGG |
| 6 | SS2_T4DNA polmismatch | ACTCCAGATGTTTCGAAACTCAAC TTGAACTCTCATCTTAGGCT |
| 7 | S53 | /5IABkFQ/AGCCTAAGATGAGAG TTCAAGTTGAGTTTGG/36-FAM/ GTTCAGTCCCTACGGCGCTAACC GCATGGCTGTTAGTGT |
| 8 | 1130048 | TAGCCCAGTTCTACGTCTACAAGC CACCGTGCTACAACCAAG/Phos GTTCAGTCCCTACGGCGCTAACT GGCCCTTAGTGTTAGT |
| 9 | 1108640 | CAACTCTACGTCTAGGGCTCAAT GCCACCGTGCTACAACCAAG/Phos |

The abbreviation nomenclature used above in the sequences is: N is A, C, G, or T nucleotide; /5Phos/ is 5'-phosphate; /5IABkFQ/ = 5'-Iowa Black Fluorescence Quencher; /iFluorT/ is an internal FAM fluorophore; /56-FAM/ is a 5'-FAM fluorophore; /36-FAM/ is a 3'-FAM fluorophore; /Phos is a 3'-phosphate. All sequences are shown 5'→3'.

Example 2

Polymerase Inhibition Assay

This example demonstrates the ability of the 120 selected aptamers to inhibit the polymerase's (PFU-sso7d or Phusion) polymerase activity.

The substrate consists of an oligonucleotide containing an internal nucleotide-linked fluorophore and a 5'-dark quencher (see Table 1, SEQ ID NO: 5). In the native confirmation, the hairpin substrate exhibits little to no fluorescence due to quenching via fluorescence resonance energy transfer (FRET). In the presence of an active polymerase, extension will occur from the primer (SEQ ID NO: 4) and the hairpin will unfold, resulting in an increase in quantifiable fluorescence. Different molar ratios (1:3, 1:5, 1:10, 1:20, and 1:30) of Phusion:aptamer complexes were tested to check for its inhibitory activity against both polymerase and exonuclease domain. The selected aptamers were first folded in polymerase storage buffer at 95° C. for 5 minutes, then snap-cooled at 4° C. for 10 mins and 25° C. for 10 mins and then incubated with the polymerase at room temperature for 1 hour. To assess inhibition, 0.2 μM PE_pol_Inhib_1 (SEQ ID NO: 5), 0.2 μM PE_pol_Inhib_ FOR (SEQ ID 4), 0.8 mM total dNTPs, 0.02 U/μL hot start Phusion polymerase, and 1× HiFi Buffer (Integrated DNA Technologies, Inc.) were mixed, on ice. Samples were run in triplicate on a Light cycler 480 at 45° C. with data acquisition every 5 seconds for a total time of 3 hours.

Example 3

Exonuclease Inhibition Assay

This example demonstrates the ability of the 120 selected aptamers to inhibit the polymerase's (PFU-sso7d or Phusion) exonuclease activity.

The substrate consists of a short oligo with fluorophore and quencher (SEQ ID NO: 7) which is hybridized to its complementary sequence (SEQ ID NO: 6). The complementary sequence contains a mismatch base-pair which gets cleaved by the exonuclease domain of the polymerase. The cleavage leads to release of the fluorophore and the activity can be measured by the change in fluorescence. To assess inhibition, 0.2 μM SS2_T4DNA pol mismatch (SEQ ID NO: 6) and 0.2 μM SS3 (SEQ ID NO: 7) were used with the same 15 folding and buffer conditions used in the polymerase inhibition assay. Samples were run in triplicate on a Light cycler 480 at 45° C. with data acquisition every 5 seconds for a total time of 3 hours.

Inhibition analysis revealed 2 candidate aptamers (SEQ ID NO: 8 and SEQ ID NO: 9). 90% of polymerase activity and 70% of exonuclease activity was inhibited by Seq 118640 (SEQ ID NO: 9). Whereas sequence 1130048 (SEQ ID NO: 8) resulted in 70% inhibition of polymerase and exonuclease activity. (See FIG. 1). Inhibition tests were performed at 1:3 (polymerase to aptamer) molar ratio (FIG. 1). Percent inhibition was calculated by dividing the background subtracted relative fluorescent units of the hot start sample at cycle 60 by the background subtracted relative fluorescent units of the no aptamer sample (polymerase only) at cycle 60 and multiplying by 100 to convert to a percentage (%).

As shown in FIG. 1 SEQ ID NO: 8 and SEQ ID NO: 9 inhibit polymerase activity (up to 80%) and exonuclease activity (up to 70%) at 45° C. and 30° C.

The temperature where the aptamer dissociates from the DNA polymerase is greater than 45° C. In some aspects, the dissociation temperature is 45-60° C., including all integers within the range. In some aspect, the dissociation temperature is 50-55° C., including all integers within the range. In one aspect, the dissociation temperature is 45, 46, 47, 48, 49, 50, 51, 52, 53, 54, 55, 56, 57, 58, 59, or 60° C.

---

What is claimed:

1. A composition comprising:
a thermostable DNA polymerase and an aptamer;
wherein the aptamer is selected from a nucleotide sequence comprising at least 90% identity to SEQ ID NO:8 or SEQ ID NO:9.

2. The composition of claim 1, wherein the aptamer is selected from a nucleotide sequence comprising SEQ ID NO:8 or SEQ ID NO:9.

3. The composition of claim 1, wherein the thermostable DNA polymerase is a Phusion DNA polymerase.

4. The composition of claim 2 wherein the Phusion DNA polymerase is Pfu-sso7d.

5. An aptamer selected from a nucleotide sequence comprising at least 90% identity to SEQ ID NO:8 or SEQ ID NO:9.

6. The aptamer of claim 5, wherein the aptamer is selected from a nucleotide sequence comprising SEQ ID NO:8 or SEQ ID NO:9.

7. A method for amplifying a target DNA sequence, said method comprising the steps of:
(a) providing a reaction mixture comprising:
(i) a thermostable DNA polymerase,
(ii) a thermostable DNA polymerase aptamer selected from a nucleotide sequence comprising at least 90% identity to SEQ ID NO:8 or SEQ ID NO: 9, wherein the thermostable DNA polymerase aptamer binds to the thermostable DNA polymerase to form a blocked thermostable DNA polymerase;

(iii) at least one oligonucleotide primer,
(iv) one or more sample nucleic acids that may or may not comprise a target sequence complementary to the at least one oligonucleotide primer;
(b) hybridizing the at least one oligonucleotide primer to the sample nucleic acids that comprise a target DNA sequence complementary to the at least one oligonucleotide primer;
(c) elevating the temperature to release the thermostable DNA polymerase aptamer from the blocked thermostable DNA polymerase; and
(d) initiating DNA polymerase activity and extending the primer with the DNA polymerase.

8. The method of claim 7, wherein the thermostable DNA polymerase aptamer is selected from a nucleotide sequence comprising SEQ ID NO:8 or SEQ ID NO:9.

9. The method of claim 7, wherein the thermostable DNA polymerase is a Phusion DNA polymerase.

10. The method of claim 9, wherein the Phusion DNA polymerase is Pfu-sso7d.

11. The method of claim 7, wherein the elevated temperature to release the thermostable DNA polymerase aptamer from the blocked thermostable DNA polymerase is greater than 45° C.

12. The method of claim 7, wherein the elevated temperature to release the thermostable DNA polymerase aptamer from the blocked thermostable DNA polymerase is from 50-55° C.

13. The method of claim 7, wherein the initiating DNA polymerase activity and extending the primer with the DNA polymerase is performed at a temperature of greater than 65° C.

14. The method of claim 7, wherein the reaction mixture further comprises, a buffer mixture and dNTPs.

15. The method of claim 14, wherein:

the buffer mixture comprises: 10 mM Tris-HCl (pH 8.4 at 25° C.), 1.5 mM MgCl$_2$, 110 mM KCl, 0.08% (w/v) Brij-58, 0.2% (w/v) PEG-8000, and 0.1% (v/v) propylene glycol); and the dNTPs comprise 0.8 mM dNTPs.

* * * * *

SEQUENCE LISTING

```
Sequence total quantity: 9
SEQ ID NO: 1            moltype = DNA  length = 82
FEATURE                Location/Qualifiers
source                 1..82
                       mol_type = other DNA
                       organism = synthetic construct
SEQUENCE: 1
gttcagtccc tacggcgcta acnnnnnnnn nnnnnnnnnn nnnnnnnnnn nnnnnnnnnn  60
nngccaccgt gctacaacca ag                                          82

SEQ ID NO: 2            moltype = DNA  length = 22
FEATURE                Location/Qualifiers
source                 1..22
                       mol_type = other DNA
                       organism = synthetic construct
misc_feature           1
                       note = 5-FAM fluorophore
SEQUENCE: 2
gttcagtccc tacggcgcta ac                                          22

SEQ ID NO: 3            moltype = DNA  length = 20
FEATURE                Location/Qualifiers
source                 1..20
                       mol_type = other DNA
                       organism = synthetic construct
misc_feature           1
                       note = 5- phosphate moiety
SEQUENCE: 3
cttggttgta gcacggtggc                                             20

SEQ ID NO: 4            moltype = DNA  length = 18
FEATURE                Location/Qualifiers
source                 1..18
                       mol_type = other DNA
                       organism = synthetic construct
SEQUENCE: 4
tctccaagtt gtggcgtc                                               18

SEQ ID NO: 5            moltype = DNA  length = 56
FEATURE                Location/Qualifiers
source                 1..56
                       mol_type = other DNA
                       organism = synthetic construct
misc_feature           1
                       note = 5-Iowa Black Fluorescence Quencher
misc_feature           23
                       note = Internal FAM Fluorophore (iFluorT)
SEQUENCE: 5
tcctcctctt tttttgagga ggtcttggta aacgatcgga cgccacaact tgcaga      56

SEQ ID NO: 6            moltype = DNA  length = 83
```

-continued

```
FEATURE                 Location/Qualifiers
source                  1..83
                        mol_type = other DNA
                        organism = synthetic construct
SEQUENCE: 6
aactagaaca ttgataattt tactggcgat gtcaatagga ctccagatgt ttcgaaactc    60
aacttgaact ctcatcttag gct                                            83

SEQ ID NO: 7            moltype = DNA   length = 31
FEATURE                 Location/Qualifiers
source                  1..31
                        mol_type = other DNA
                        organism = synthetic construct
misc_feature            1
                        note = 5-Iowa Black Fluorescence Quencher
misc_feature            31
                        note = 3-FAM fluorophore
SEQUENCE: 7
agcctaagat gagagttcaa gttgagtttg g                                   31

SEQ ID NO: 8            moltype = DNA   length = 81
FEATURE                 Location/Qualifiers
source                  1..81
                        mol_type = other DNA
                        organism = synthetic construct
misc_feature            81
                        note = 3-phosphate moiety
SEQUENCE: 8
gttcagtccc tacggcgcta accgcatggc tgttagtgtt agcccagttc tacgtctaca    60
agccaccgtg ctacaaccaa g                                              81

SEQ ID NO: 9            moltype = DNA   length = 82
FEATURE                 Location/Qualifiers
source                  1..82
                        mol_type = other DNA
                        organism = synthetic construct
misc_feature            82
                        note = 3-phosphate moiety
SEQUENCE: 9
gttcagtccc tacggcgcta actggccctt agtgttagtc aactctacgt ctagggctca    60
atgccaccgt gctacaacca ag                                             82
```